(12) United States Patent
Lin et al.

(10) Patent No.: US 11,311,715 B2
(45) Date of Patent: Apr. 26, 2022

(54) SELF-POWERED SHEET

(71) Applicant: CYMMETRIK ENTERPRISE CO., LTD., Taipei (TW)

(72) Inventors: Wen-An Lin, Taipei (TW); Che-Ling Chang, Taipei (TW)

(73) Assignee: CYMMETRIK ENTERPRISE CO., LTD., Taipei (TW)

( * ) Notice: Subject to any disclaimer, the term of this patent is extended or adjusted under 35 U.S.C. 154(b) by 334 days.

(21) Appl. No.: 16/159,066

(22) Filed: Oct. 12, 2018

(65) Prior Publication Data

US 2020/0114143 A1 Apr. 16, 2020

(51) Int. Cl.
*A61N 1/04* (2006.01)
*A61N 1/30* (2006.01)

(52) U.S. Cl.
CPC ............. *A61N 1/0428* (2013.01); *A61N 1/30* (2013.01)

(58) Field of Classification Search
CPC .......... A61M 37/00; A61M 2037/0007; A61M 2205/0233; A61N 1/0428; A61N 1/0432; A61N 1/0436; A61N 1/0444; A61N 1/30; A61N 1/303; A61N 1/325; A61N 1/0448; A61N 1/0476
See application file for complete search history.

(56) References Cited

U.S. PATENT DOCUMENTS

| 5,405,317 | A | * | 4/1995 | Myers | .................. | A61N 1/0436 604/20 |
|---|---|---|---|---|---|---|
| 2005/0187580 | A1 | | 8/2005 | Skiba | | |
| 2007/0060862 | A1 | | 3/2007 | Sun et al. | | |
| 2010/0010418 | A1 | * | 1/2010 | Nisato | .................... | A61K 47/32 604/20 |

FOREIGN PATENT DOCUMENTS

CN 104225787 A 12/2014

OTHER PUBLICATIONS

Procellera with PROSIT Technology Scientific Summary, VOMARIS; Aug. 2010.

* cited by examiner

*Primary Examiner* — Shefali D Patel
(74) *Attorney, Agent, or Firm* — Maschoff Brennan

(57) ABSTRACT

The disclosure provides a self-powered sheet which is configured to absorb a liquid content and to be applied on a human skin. The self-powered sheet includes a base layer and a plurality of electrically conductive inks. The base layer is configured to absorb the liquid content and adapted to be applied on the human skin. The base layer has a contact surface. The electrically conductive inks are disposed on the contact surface of the base layer. Each of the electrically conductive inks has a plurality of first electrodes and a plurality of second electrodes. When each of the first electrodes and each of the second electrodes are soaked in the liquid content, an electrical potential difference between one of the plurality of first electrodes and one of the plurality of second electrodes generates a current in the human skin.

5 Claims, 4 Drawing Sheets

SELF-POWERED SHEET

TECHNICAL FIELD

The disclosure relates to a self-powered sheet.

BACKGROUND

A facial mask is a common skin care treatment that can hydrate the skin. It often contains minerals, vitamins, and fruit extracts for different purposes; some are for cleaning the pores, and some are for moisturizing and nourishing the skin.

As the facial mask develops, there is an electric facial mask in the market; it utilizes current to massage the facial skin. In detail, the conventional electric facial mask is manufactured by printing inks on a sheet so as to apply two types of electrodes to the sheet. However, each ink only contains one type of the electrodes, thus it only can print one of the types of the electrodes at a time. As a result, the manufacturing of the conventional electric facial requires to perform the printing process for two times, which is time consuming and not cost effective.

SUMMARY OF THE INVENTION

The disclosure provides a self-powered sheet which is capable of allowing two types of the electrodes to be applied to the sheet by performing a printing process for one time.

One embodiment of the disclosure provides a self-powered sheet which is configured to absorb and to be applied on a human skin. The self-powered sheet includes a base layer and a plurality of electrically conductive inks. The base layer is configured to absorb the liquid and adapted to be applied on the human skin. The base layer has a contact surface. The electrically conductive inks are disposed on the contact surface of the base layer. Each of the electrically conductive inks has a plurality of first electrodes and a plurality of second electrodes. When each of the first electrodes and each of the second electrodes are soaked in the liquid, an electrical potential difference between one of the plurality of first electrodes and one of the plurality of second electrodes generate a current in the human skin.

According to the self-powered sheet as discussed above, each electrically conductive ink has the first electrodes and the second electrodes, thus all of the first electrodes and the second electrodes are disposed on the base layer by performing the printing process for one time during a manufacturing process of the self-powered sheet. As such, compared with the first electrodes and the second electrodes respectively disposed on the base layer by performing the printing process for two times, the time and the cost in manufacturing the self-powered sheet can be reduced.

BRIEF DESCRIPTION OF THE DRAWINGS

The present disclosure will become better understood from the detailed description given herein below and the accompanying drawings which are given by way of illustration only and thus are not intending to limit the present disclosure and wherein.

DETAILED DESCRIPTION

Figure 1:
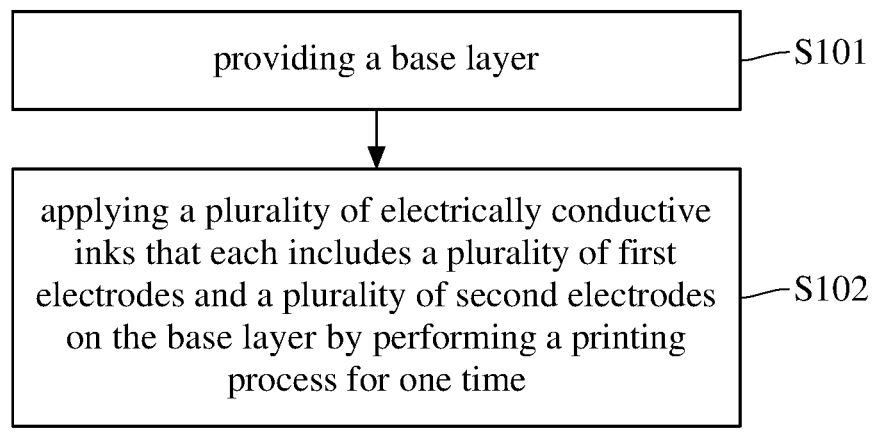
FIG. 1 is a flow chart of manufacturing a self-powered sheet according to a first embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
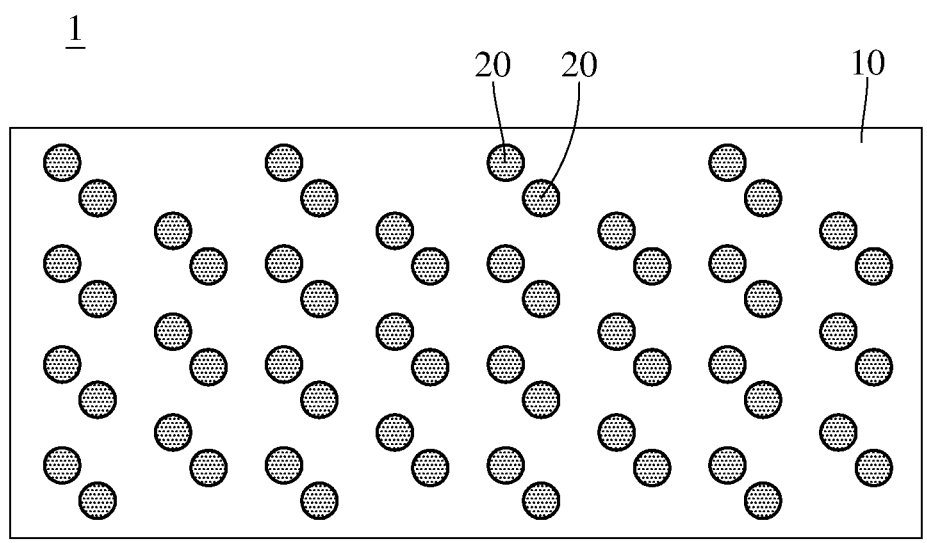
FIG. 2 is a schematic view of the self-powered sheet according to the first embodiment of the disclosure.
Figure 3:
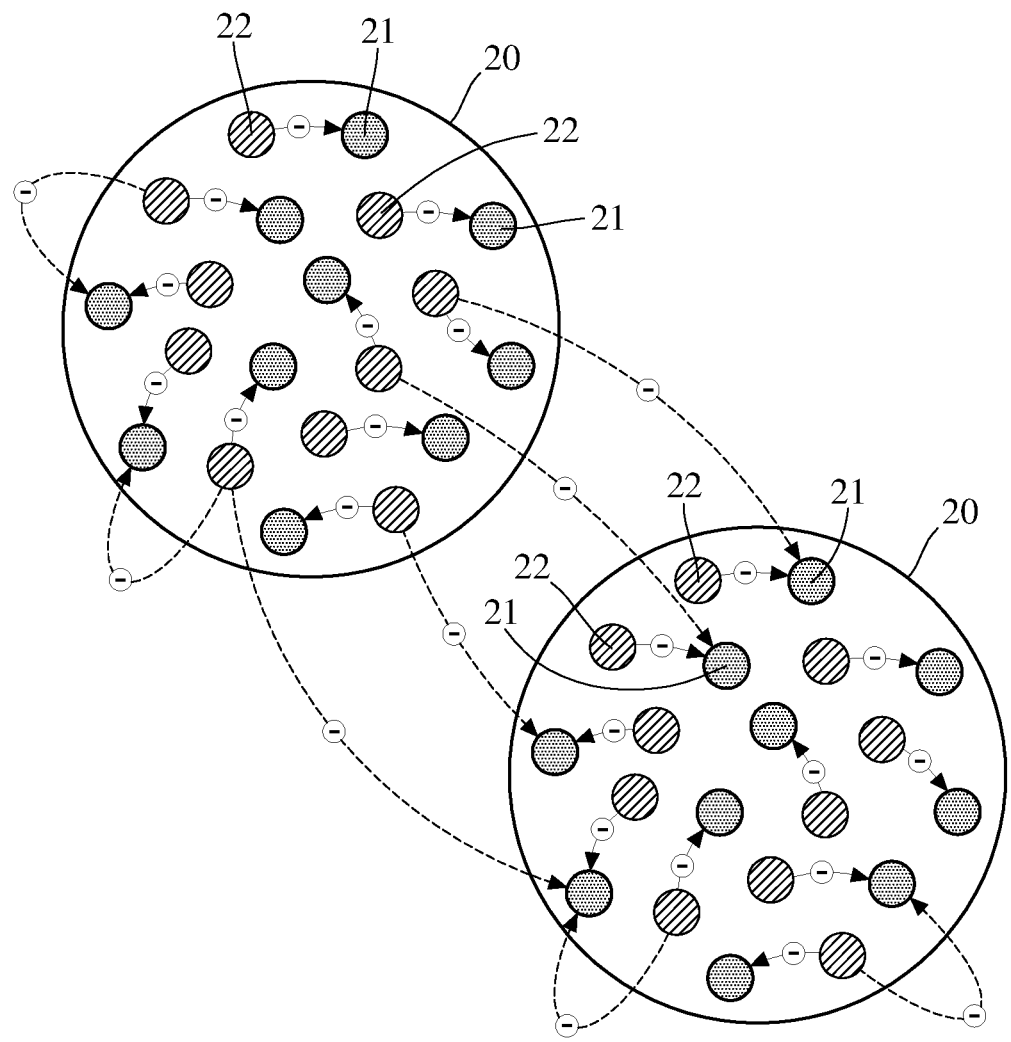
FIG. 3 is a partial enlarged schematic view of the self-powered sheet in FIG. 2.
Figure 4:
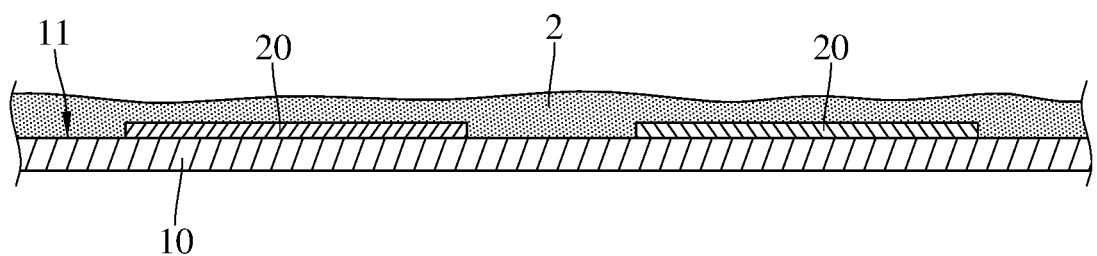
FIG. 4 is a partial enlarged cross-sectional view of the self-powered sheet in FIG. 2.

Please refer to FIG. 1 and FIG. 4. FIG. 1 is a flow chart of manufacturing a self-powered sheet according to a first embodiment of the disclosure. FIG. 2 is a schematic view of the self-powered sheet according to the first embodiment of the disclosure. FIG. 3 is a partial enlarged schematic view of the self-powered sheet in FIG. 2. FIG. 4 is a partial enlarged cross-sectional view of the self-powered sheet in FIG. 2.

This embodiment provides a self-powered sheet 1. The self-powered sheet 1 is, for example, a facial mask or a face mask. The self-powered sheet 1 is able to absorb a liquid content 2. The liquid content 2 may include a mixture of skin toner, lotion, essence and/or other skin-beneficial ingredients, but the present application is not limited thereto. The self-powered sheet 1 can be applied on the human skin (not shown in figures) to let the human skin to absorb the liquid content 2 so as to achieve the purpose of skincare. The process of manufacturing the self-powered sheet 1 and detailed structure of the self-powered sheet 1 are described in the following paragraphs.

The process of manufacturing the self-powered sheet 1 includes Steps S101 and S102. In step S101, a base layer 10 is provided. The base layer 10 is made from, for example, non-woven fabric, but the present disclosure is not limited thereto. In some other embodiments, the base layer may be made from woven fabric. Furthermore, in other embodiments, the base layer may be made of polymeric material, rubber, cotton or other soft plastic materials such as polyurethane (PU), polyethylene (PE), polyethylene terephthalate (PET), thermoplastic polyurethane (TPU) and thermoplastic polyester elastomer (TPEE). In another embodiment, the base layer may be a mixture of fibers and powders. The powders are optional and may contain, for example, charcoal, chitin or negative ion. The base layer 10 is able to absorb the liquid content 2 and to be applied on the human skin. In this embodiment, the base layer 10 has a contact surface 11.

Then, in step S102, a plurality of electrically conductive inks 20 that each includes a plurality of first electrodes 21 and a plurality of second electrodes 22 are applied on the base layer 10 by performing a printing process for one time. In more detail, the electrically conductive inks 20 are applied on the contact surface 11 of the base layer 10, for example, by a screen printing process, an intaglio printing process, a flexographic printing process or a digital printing process, and the plural first electrodes 21 and second electrodes 22 in each electrically conductive ink 20 are all made of electrically conductive materials. When the first electrodes 21 and the second electrodes 22 are soaked in the liquid content 2, each first electrode 21 and the adjacent second electrodes 22 have electrical potential differences therebetween, vice versa. In one example, the first electrodes 21 are silver, and the second electrodes 22 are zinc, they have a different electric potential, and their resistances both fall within $10^{-1}\Omega$ to $10^{3}\Omega$.

Then, by immersing the self-powered sheet 1 into the liquid content 2 or spraying the liquid content 2 on the self-powered sheet 1, the liquid content 2 can be absorbed by and fixed on the self-powered sheet 1. During the process, due to the liquid content 2, the first electrodes 21 and the second electrodes 22 in each electrically conductive ink 20 respectively create electrical potential differences therebetween, and the first electrodes 21 and the second electrodes 22 among the adjacent the electrically conductive inks 20 also create electrical potential differences therebetween.

Then, the combination of the liquid content 2 and the self-powered sheet 1 can be applied on the human skin by placing the contact surface 11 of the base layer 10 on the human skin, such that the first electrodes 21 and the second electrode 22 are in contact with the human skin. At this moment, a circuit is formed by the human skin, the first electrodes 21, and the second electrodes 22, such that a current is produced in the human skin due to the electrical potential differences between the first electrodes 21 and the second electrodes 22, thereby accelerating the process of absorbing the liquid content 2 by the human skin.

The materials of the first electrodes 21 and the second electrodes 22 are not restricted as long as that the first electrode and second electrode are different in electric potential. For example, in some other embodiments, the first electrodes and the second electrodes may include at least one material selected from a group consisting of zinc (Zn), copper (Cu), silver (Ag), and carbon (C).

In this embodiment, each electrically conductive ink 20 has the first electrodes 21 and the second electrodes 22, thus all of the first electrodes 21 and the second electrodes 22 are disposed on the base layer 10 by performing the printing process for one time during a manufacturing process of the self-powered sheet 1. As such, compared with the first electrodes and the second electrodes respectively disposed on the base layer by performing the printing process for two times, the time and the cost in manufacturing the self-powered sheet 1 can be reduced.

In detail, in terms of the first electrodes and the second electrodes respectively disposed on the base layer by performing the printing process for two times, while printing the second electrodes on the base layer after the first electrodes have been printed on the base layer, the base layer would shrink and cause a part of the first electrodes to contact a part of the second electrodes. Therefore, before printing the first electrodes and the second electrodes on the base layer, it requires to let the base layer to shrink to a stable state and to preposition the places where to print the first electrodes and the second electrodes on the base layer. In the case of disposing the first electrodes and second electrodes on a 300-meter long base layer, the aforementioned processes cause the time of disposing these electrodes up to 6.3 hours.

In contrast, in the embodiment, of the present disclosure, since the electrically conductive inks 20 each have the first electrodes 21 and the second electrodes 22, and the base layer would not cause the first electrodes 21 to contact the second electrodes 22 during the printing process, thus there is no need to shrink the base layer 10 and to preposition the places for the first electrodes 21 and the second electrodes 22. Therefore, using the electrically conductive inks 20 is time-saving. And it only costs 1 hour to dispose the first electrodes 21 and the second electrodes 22 on a 300-meter-long base layer.

Figure 5:
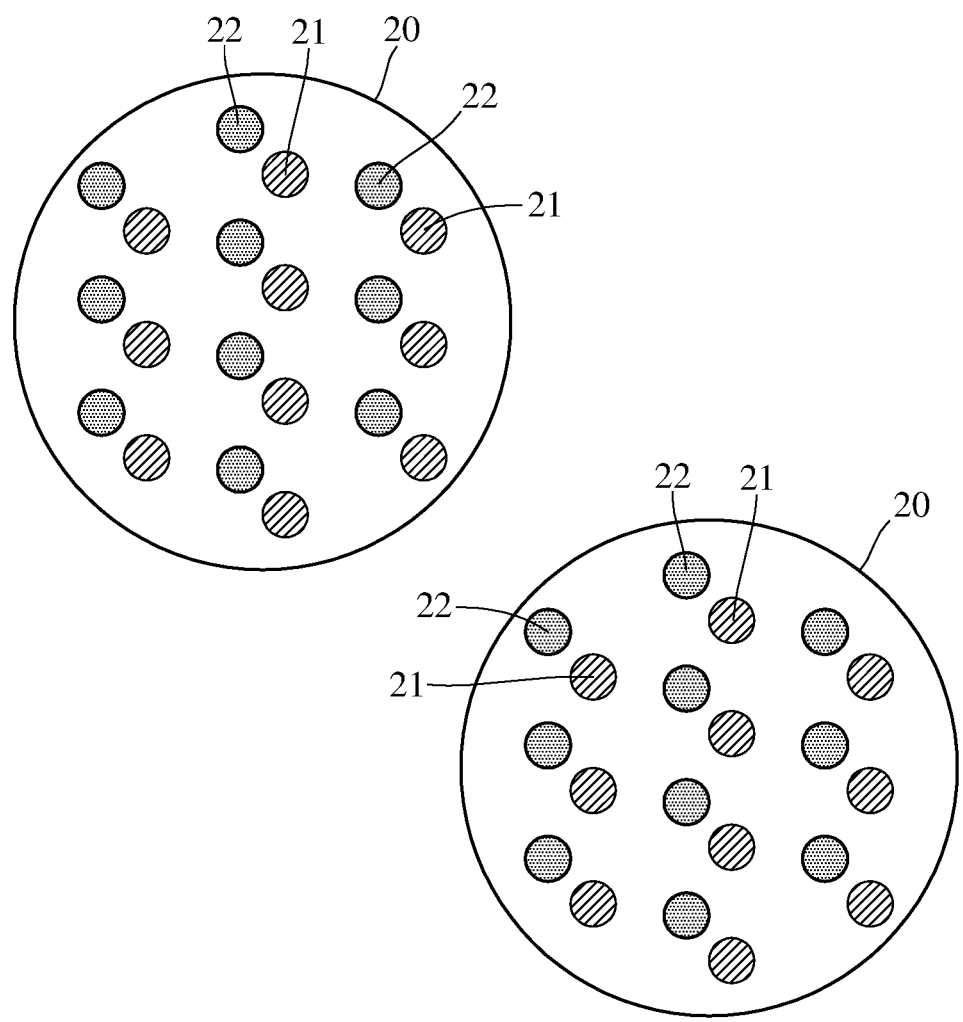
FIG. 5 is a partial enlarged schematic view of a self-powered sheet according to a second embodiment of the disclosure.

In FIG. 3, the first electrodes 21 and the second electrodes 22 in each electrically conductive ink 20 are arranged irregularly, but the present disclosure is not limited thereto. Please refer to FIG. 5. FIG. 5 is a partial enlarged schematic view of a self-powered sheet according to a second embodiment of the disclosure. In FIG. 5, the first electrodes 21 and second electrodes 22 in each electrically conductive ink 20 are arranged in a staggered manner.

Figure 6:
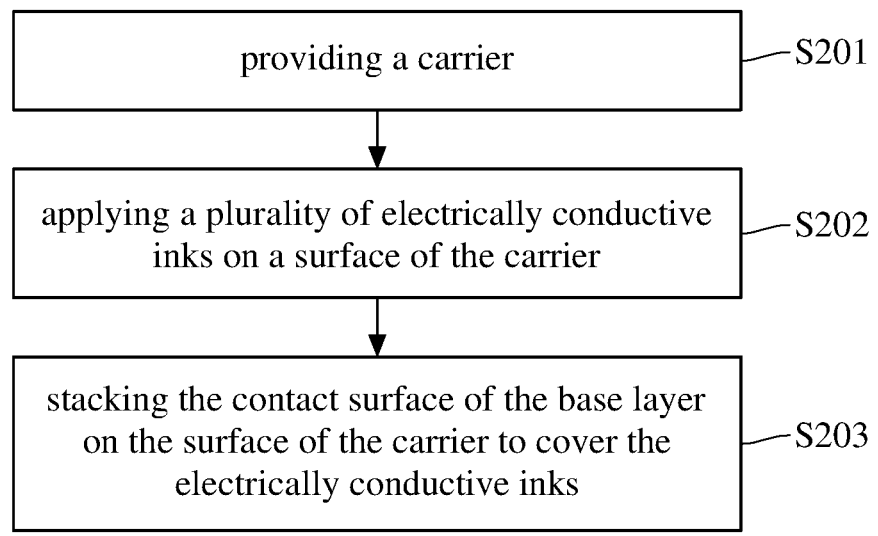
FIG. 6 is a flow chart of manufacturing a self-powered sheet according to a third embodiment of the disclosure.
Figure 7:
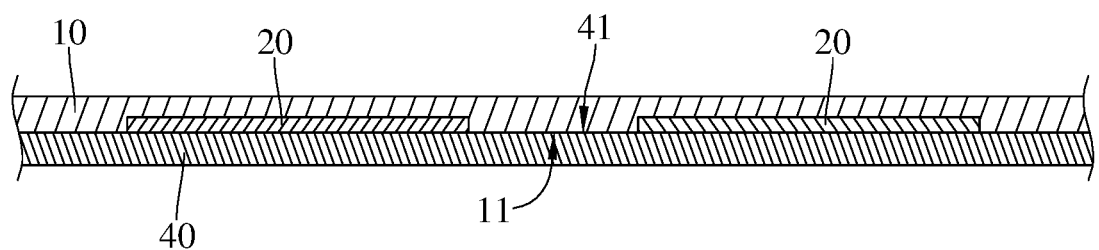
FIG. 7 is a partial enlarged cross-sectional view of the self-powered sheet according to the third embodiment of the disclosure.

In the aforementioned embodiments, the electrically conductive inks 20 are directly applied on the contact surface 11 of the base layer 10, but the present disclosure is not limited thereto. For example, please refer to FIG. 6 and FIG. 7. FIG. 6 is a flow chart of manufacturing a self-powered sheet according to a third embodiment of the disclosure. FIG. 7 is a partial enlarged cross-sectional view of the self-powered sheet according to the third embodiment of the disclosure.

The process of manufacturing the self-powered sheet of this embodiment includes Steps S201 to S203.

In S201, a carrier 40 is provided. The carrier 40 is, for example, made of PU, but the present disclosure is not limited thereto. In some other embodiments, the carrier may be made of another plastic material such as PE, PET, TPU or TPEE.

Then, in step S202, the electrically conductive inks 20 are applied on a surface 41 of the carrier 40. In this embodiment, the electrically conductive inks 20 are applied on the surface 41 of the carrier 40 by performing a printing process for one time. The printing process is the same as that of the first embodiment, and the materials of the first electrodes 21 and the second electrodes 22 are the same as that of the first embodiment.

Then, in step S203, the contact surface 11 of the base layer 10 is stacked on the surface 41 of the carrier 40 such that the electrically conductive inks 20 are covered by and located between the contact surface 11 of the base layer 10 and the surface 41 of the carrier 40. As a result, the electrically conductive inks 20 are disposed on the base layer 10.

In the case that the base layer 10 is made from, for example, non-woven fabric, the base layer 10 is thin and stretchable, and the carrier 40 can help the electrically conductive inks 20 to be disposed on the base layer 10.

According to the self-powered sheet as discussed above, each electrically conductive ink includes the first electrodes and the second electrodes, thus all of the first electrodes and the second electrodes are disposed on the base layer by performing the printing process for one time during the manufacturing process of the self-powered sheet. As such, compared with the first electrodes and the second electrodes respectively disposed on the base layer by performing the printing process for two times, the time and the cost in manufacturing the self-powered sheet can be reduced.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A self-powered sheet, configured to absorb a liquid content and to be applied on a human skin, comprising:

a base layer made of an absorbent material and configured to absorb the liquid content and adapted to be applied on the human skin, and the base layer having a contact surface;

a plurality of electrically conductive ink layers disposed on the contact surface of the base layer and separated from one another, each of the plurality of electrically conductive ink layers separated from one another comprising a plurality of first electrodes and a plurality of second electrodes; and when each of the plurality of first electrodes and each of the plurality of second electrodes are soaked in the liquid content, an electrical potential difference between one of the plurality of first electrodes and one of the plurality of second electrodes only generates a current in the human skin; and a carrier, wherein the carrier has a surface, the plurality of electrically conductive ink layers are printed on the surface of the carrier, the contact surface of the base layer is stacked on the surface of the carrier so that the plurality of electrically conductive ink layers are covered by the base layer made of the absorbent material and the carrier;

wherein the plurality of first electrodes and the plurality of second electrodes are made of different materials, and each of the plurality of first electrodes and each of the plurality of second electrodes are different in electric potential.

2. The self-powered sheet according to claim 1, wherein the carrier is made of polyurethane, polyethylene, polyethylene terephthalate, thermoplastic polyurethane or thermoplastic polyester elastomer.

3. The self-powered sheet according to claim 1, wherein the plurality of first electrodes and the plurality of second electrodes of each of the plurality of electrically conductive ink layers are arranged in a staggered manner.

4. The self-powered sheet according to claim 1, wherein each of the plurality of first electrodes and each of the plurality of second electrodes comprise at least one material selected from a group consisting of zinc (Zn), copper (Cu), silver (Ag), and carbon (C).

5. The self-powered sheet according to claim 4, wherein the plurality of first electrodes are made of silver, and the plurality of second electrodes are made of zinc.

\* \* \* \* \*